United States Patent [19]

Mochizuki

[11] Patent Number: 4,969,363
[45] Date of Patent: Nov. 13, 1990

[54] ELECTROMAGNETIC FLOWMETER CAPABLE OF SIMULTANEOUS MEASUREMENT OF FLOW RATE AND CONDUCTIVITY OF FLUID

[75] Inventor: Tsutomu Mochizuki, Okazaki, Japan

[73] Assignee: Aichi Tokei Denki Co., Ltd., Aichi, Japan

[21] Appl. No.: 329,714

[22] Filed: Mar. 28, 1989

[30] Foreign Application Priority Data

Mar. 29, 1988 [JP] Japan .................. 63-75120

[51] Int. Cl.⁵ .............................................. G01F 1/60
[52] U.S. Cl. .................................... 73/861.17; 324/439
[58] Field of Search ........... 73/861.12, 861.16, 861.17, 73/198; 324/439

[56] References Cited

U.S. PATENT DOCUMENTS 3,290,585 12/1966 McHowell ..................... 324/439 X
3,896,373 7/1975 Zelby ............................. 324/439 X
3,999,443 12/1976 Appel et al. .
4,676,112 6/1987 Uematsu et al. ................. 73/861.17

FOREIGN PATENT DOCUMENTS 56-21015 2/1981 Japan .
59-174718 10/1984 Japan .
63-6420 1/1988 Japan .
805069 2/1981 U.S.S.R. .

Primary Examiner—Charles A. Ruehl
Attorney, Agent, or Firm—Pollock, Vande Sande & Priddy

[57] ABSTRACT

In an electromagnetic flowmeter one of two electrodes mounted on a measuring pipe is impressed with an electrical pulse synchronous with the switching of an excitation currrent, thereby detecting the voltage drop across the electrical resistance of a fluid, such that both the conductivity and the flow rate of the fluid are measureable at the same time.

12 Claims, 8 Drawing Sheets

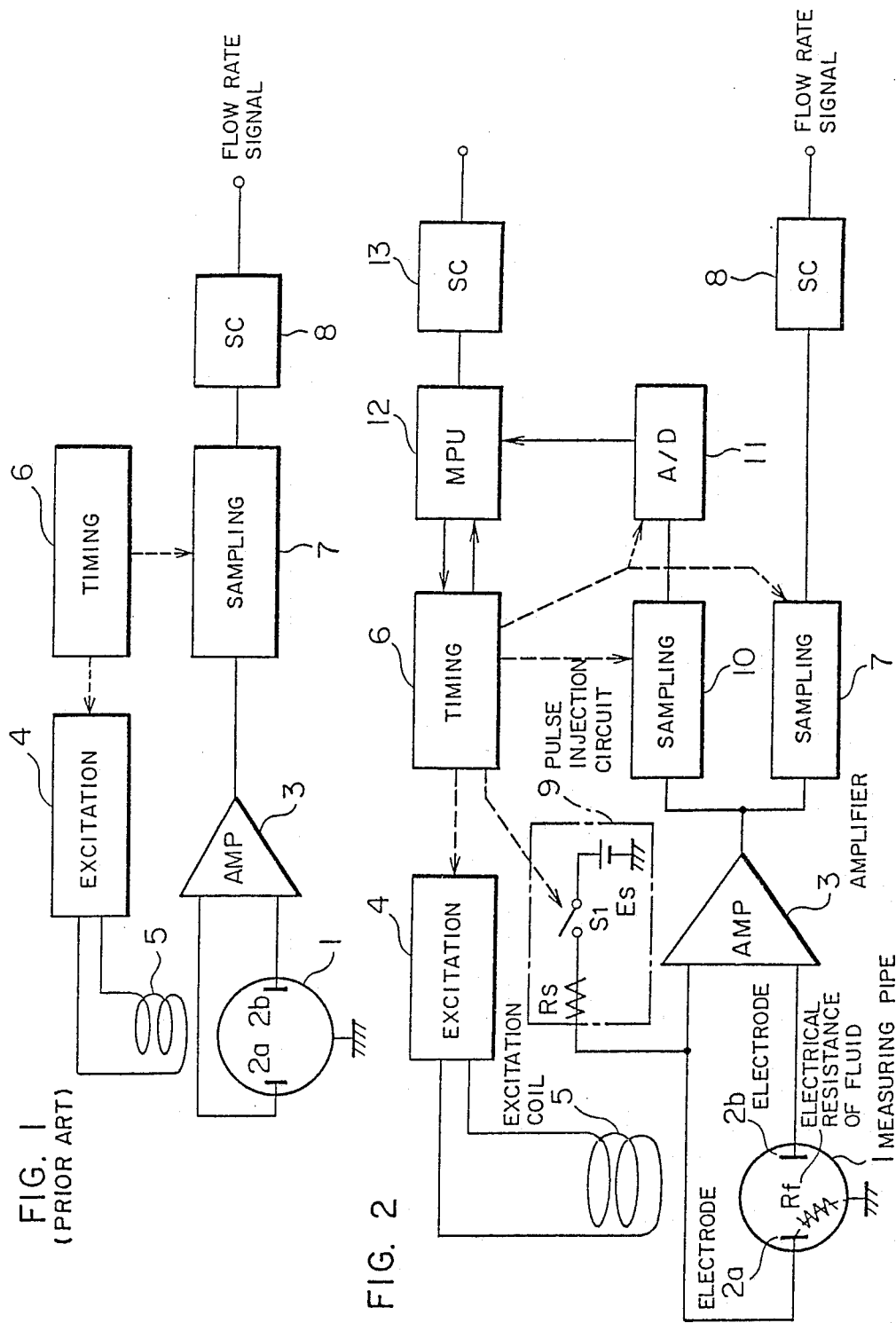

FIG. 3E
OUTPUT OF SAMPLING 10 (CONDUCTIVITY SIGNAL)
FIG. 3F
OUTPUT OF SAMPLING 7 (FLOW RATE SIGNAL)
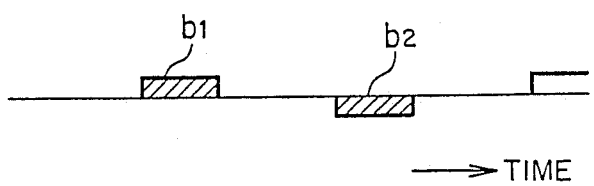
→ TIME
FIG. 4
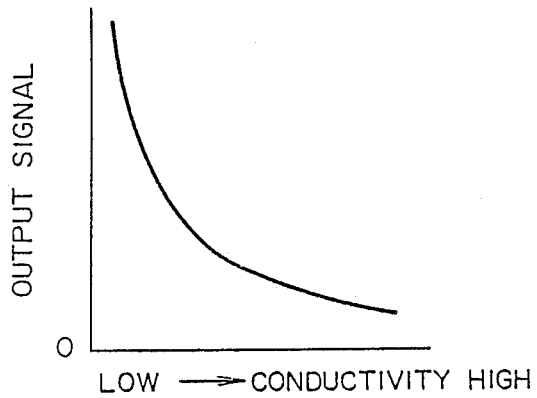

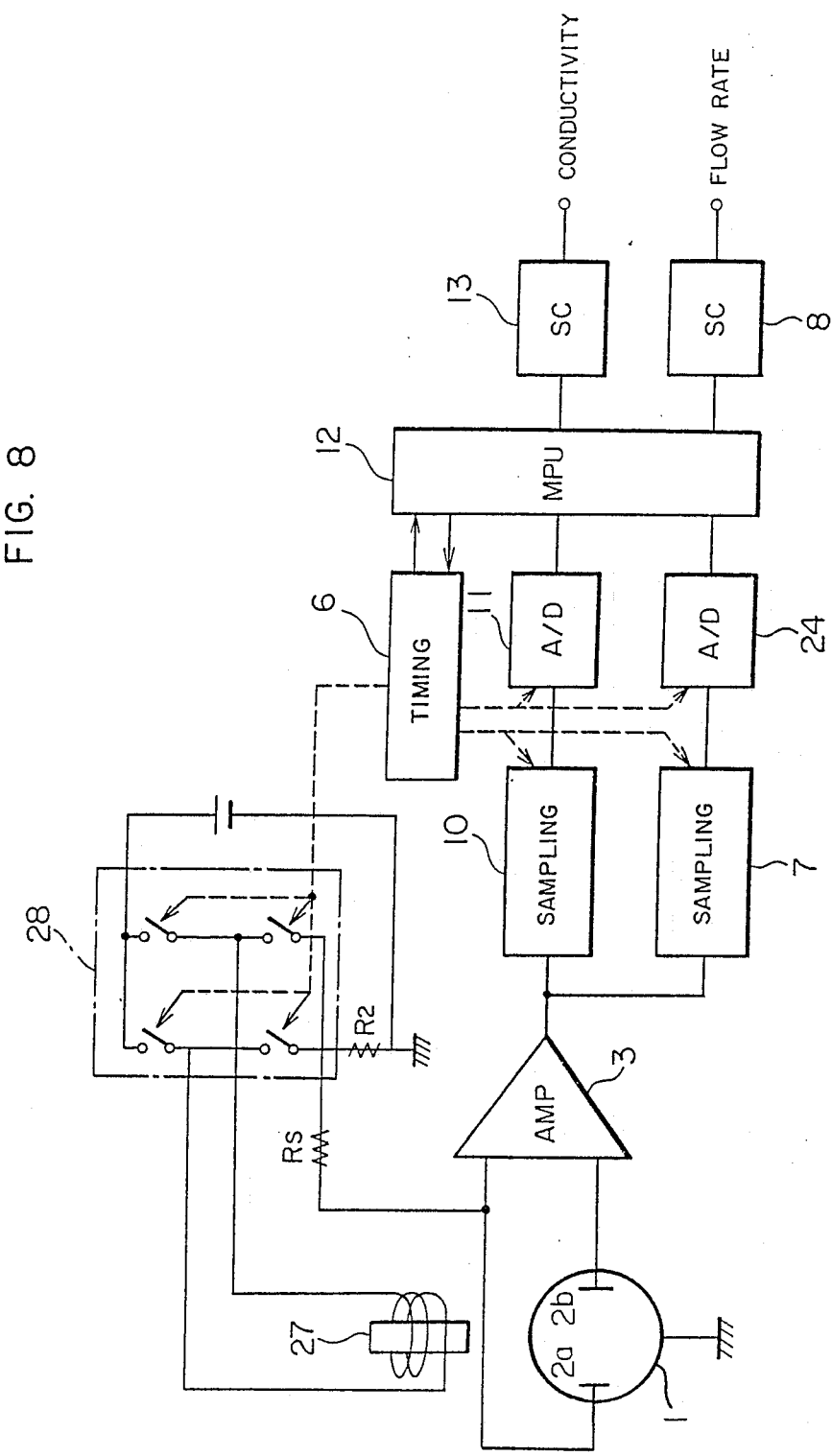

FIG. 10A
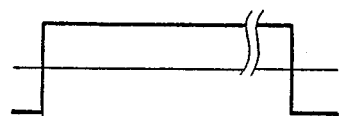
FIG. 10B
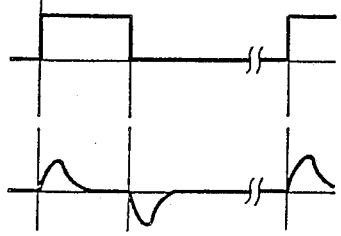
FIG. 10C

4,969,363

ELECTROMAGNETIC FLOWMETER CAPABLE OF SIMULTANEOUS MEASUREMENT OF FLOW RATE AND CONDUCTIVITY OF FLUID

BACKGROUND OF THE INVENTION

The present invention relates to an electromagnetic flowmeter for simultaneously measuring the flow rate and the conductivity of a fluid.

A flowmeter, such as an electromagnetic flowmeter, is used to measure a conductive fluid. In recent years, demand has also increased for information as to the characteristics of a fluid, such as conductivity, in addition to the flow rate thereof.

Conventional electromagnetic flowmeters which only measure the flow rate, for example, as disclosed in JPA-63-6420 and as shown in FIG. 1, require a separate measuring instrument if the conductivity of a fluid is to be measured, thereby complicating the construction of the entire system.

In the flowmeter shown in FIG. 1, a fluid flows in a measuring pipe 1. An excitation coil 5 is excited by a pulse excitation current generated in an excitation circuit which is controlled by a timing circuit 6, and the resulting magnetic fluxes are applied in a direction substantially perpendicular to the flow of the fluid. A voltage induced within the fluid by the magnetic fluxes is detected by a pair of electrodes 2a, 2b, and after being amplified by an amplifier 3 and sampled by a sampling circuit 7, an output signal representing a flow rate is produced at an output circuit 8.

In this electromagnetic flowmeter, detection of the conductivity of a fluid, such as the degree of turbidity of water, requires separate, exclusive measuring means, thereby complicating configuration of the entire system and increasing a product cost.

SUMMARY OF THE INVENTION

Accordingly, an object of the present invention is to provide an electromagnetic flowmeter slightly changed in configuration which can simultaneously measure both the flow rate and the conductivity of a fluid.

Another object of the invention is to provide an electromagnetic flowmeter with means for detecting whether a measuring pipe is not filled with fluid.

Still another object of the invention is to provide an electromagnetic flowmeter which consumes less power.

In order to achieve the first object, an electromagnetic flowmeter, according to the present invention, comprises means for generating magnetic fluxes in a direction perpendicular to the direction of fluid flow in a measuring pipe and a pair of electrodes positioned in the measuring tube in contact with the fluid for detecting an induced voltage generated in the fluid by the flow thereof, wherein an electric pulse synchronous with the switching of an excitation current is supplied between one of the electrodes and the earth and a voltage drop across the electrical resistance of the fluid is detected by the electrical pulse, thus producing a flow rate signal and a conductivity signal associated with the flow rate and the conductivity of the fluid, respectively.

The second object of the invention is achieved in such a manner that the voltage drop across the electrical resistance of the fluid is amplified and compared with a reference voltage to detect whether the measuring tube in not filled with fluid if the voltage drop exceeds the reference voltage level.

Further, in order to achieve the third object of the invention, the excitation magnetic field is adapted to increase with the decrease in conductivity.

In view of the fact that an electrical impulse synchronous with an excitation current is supplied between one of a pair of electrodes and the earth for detecting an induced voltage corresponding to the velocity of a fluid, the voltage drop caused across the electrical resistance of the fluid between the particular electrode and the earth corresponds to the conductivity of the fluid. As a result, it is possible to produce a flow rate signal simultaneously associated with the velocity of the fluid and a conductivity signal associated with the conductivity of the fluid.

In the case where the fluid does not quite fill the measuring pipe and the electrodes supplying the electrical impulse are exposed, the voltage drop remarkably increases. If this voltage drop is compared with a reference voltage, therefore, it is possible to detect whether the fluid does not quite fill the measuring tube.

Further, the excitation magnetic field is normally kept low in intensity and is increased with the decrease in conductivity. If the conductivity of a fluid is small, the fluctuation of the flow rate signal, i.e. the induced voltage associated with the flow velocity, is increased with the reduction of S/N. If a reduced conductivity of fluid is detected from the change in the conductivity signal and the excitation magnetic field is intensified, the flow rate signal is increased, thereby reducing the influence of the fluctuation of the flow rate signal. The magnitude of flow rate signal is proportional to the magnetic field, and the fluctuation is inversely proportional to the conductivity. An electromagnetic flowmeter with a low average power consumption is achieved.

BRIEF DESCRIPTION OF THE DRAWINGS

FIG. 1 is a block circuit diagram showing a conventional electromagnetic flowmeter;

FIG. 2 is a block circuit diagram showing an embodiment of the present invention;

FIGS. 3A–F are graphs explaining the operation of the embodiment shown in FIG. 2;

FIG. 4 is a graph indicating the relationship between the conductivity of a fluid and an output signal;

FIG. 8 is a block circuit diagram showing a fifth embodiment comprising an electromagnetic flowmeter section of the residual magnetism type;

FIGS. 10A to 10C are diagrams showing waveforms of operation corresponding to A to C of FIG. 9, respectively.

DESCRIPTION OF THE PREFERRED EMBODIMENTS

Figure 3A:
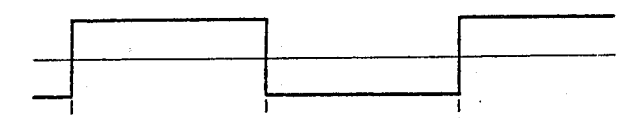

One embodiment of the present invention is shown in FIG. 2. Reference numeral 1 designates a measuring pipe through which a fluid passes and which contains a pair of electrodes 2a and 2b positioned opposite each other. Numeral 5 designates an excitation coil excited by an excitation circuit 4 to form magnetic fluxes in a direction substantially perpendicular to the flow of the fluid. A pulse injection circuit 9 includes a power supply Es with an end thereof grounded, an electronic switch S1 and a resistor Rs. An end of the resistor Rs is connected to one of the two electrodes, for example the electrode 2a. When the switch S1 is turned on for a short length of time in synchronism with the excitation current, an electrical pulse is applied only in one direction, for example, a positive direction, through the resistor Rs to the electrode 2a. The impulse voltage thus applied becomes the voltage divided by the electrical resistance Rf of the fluid between the electrode 2a and the earth and the resistor Rs, causing what is hereinafter called "the voltage drop due to the electrical resistance Rf". This voltage is detected together with the induced voltage associated with the flow velocity at the electrodes 2a, 2b. The output voltage of differential amplifier 3 is applied to two sampling circuits 7 and 10. The output of the sampling circuit 7 provides a flow rate signal, which is converted into a digital signal or an analog signal of 4 to 20 mA and produced by an output circuit 8. The output of the sampling circuit 10, on the other hand, is converted into a digital quantity by an A/D converter 11 and further into a conductivity signal by a microcomputer 12, and then produced as a digital signal or an analog signal of 4 to 20 mA, like the flow rate signal, by the output circuit 13. The pulse injection circuit 9, the excitation circuit 4, the sampling circuits 7 and 10 and the A/D converter circuit 11 are controlled by a timing circuit 6.

The timings of a series of operations are shown in FIGS. 3A to 3F.

Figure 3B:

FIG. 3A shows an excitation current flowing in the excitation coil. FIG. 3B shows the timings at which the electronic switch S1 of the pulse injection circuit 9 is turned on. The current that flows to the electrode 2a from the pulse injection circuit 9 is in the form of a pulse of a predetermined duration shorter than a half cycle of the excitation current obtained upon activation of the electronic switch S1, with the time point of excitation current change as a starting point. When it is said that a pulse duration is shorter than a half cycle, it is meant that the pulse duration is short so as not to affect the sampling region of the flow rate signal considerably, or that it is so short that the electrochemical reaction between the electrodes and the fluid can be sufficiently dampened.

Figure 3C:
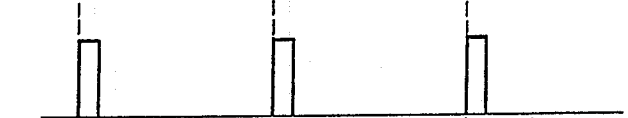
Figure 3D:
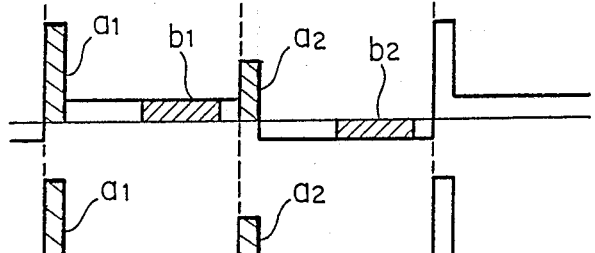

FIG. 3C shows a voltage drop caused by voltage division through the resistor Rs and the electrical resistance Rf of the fluid in the pipe. This voltage is proportional to the electrical resistance Rf between the electrodes and the earth, and as long as the fluid is flowing, a waveform as shown in FIG. 3D appears between the electrodes. More specifically, the waveform appears as a combination of the voltage drop due to the electrical resistance Rf and the induced voltage proportional to the flow velocity. A great proportion of the rise portions (a1 and a2) of the waveform is represented by the voltage drop due to the electrical resistance Rf, while the central portions (b1 and b2) are mostly associated with the flow rate signal. Since the portion a2 represents a negative flow rate signal, the waveform on which the pulse C is superimposed takes a form different from a1. Spike-like thin noises, which are developed in an output waveform due to the switching of the excitation electrodes or a pulse inflow, are not shown in FIGS. 3C and 3D.

Now, the waveform shown in FIG. 3D is sampled separately with the portions a1, a2 and b1, b2.

The result of sampling with the portions a1, a2 alone is shown in FIG. 3E, which extracts only the portions a1 and a2 which are comparatively large in the voltage drop due to the electrical resistance Rf. FIG. 3F shows only the portions b1 and b2 picked up as mainly representing the flow rat signal.

These portions a1, a2 and b1, b2 are sampled separately as output signals.

In FIG. 2, the sampling circuit 7 performs synchronous rectification which is a common method of sampling for an electromagnetic flowmeter, so that the area of the portion b1 is sampled positive while the area of the portion b2 is sampled in reverse polarity, and the results of the two samplings are added to each other. Thus, the flow rate signals at the portions b1 and b2 are increased by addition, while the minute residual voltage of the voltage drop due to the resistance Rf contained in the portions b1, b2 are in opposite electrodes and therefore are eliminated by being offset, such that only the flow rate signal is converted into an output signal at the output circuit 8.

The sampling circuit 10, on the other hand, outputs merely the sum of the areas of the portion a1 and the portion a2 to the A/D converter 11.

By so doing, the voltage drops due to the resistance Rf are added to each other, while the flow signal portions contained in a1 and a2 are opposite in polarity and are offset with each other.

As a result, only the voltage drop due to the resistance Rf is supplied to the A/D converter circuit 11.

FIG. 4 shows a rough relationship between an output signal with a voltage drop due to the resistance Rf and the conductivity of the fluid. With the increase in conductivity, the output signal is decreased, while with the decrease in conductivity, the output signal increases, thereby maintaining a fixed relationship between the voltage drop and the conductivity.

From the relationship shown in FIG. 4, the conductivity can be easily calculated by use of the microcomputer 12 shown in FIG. 2. As a consequence, both the flow rate signal and the conductivity can be measured at the same time by a single electromagnetic flowmeter. Although a configuration comprising the A/D converter 11 and the microcomputer 12 is shown in FIG. 2 as an example for the ability thereof to calculate the conductivity and issue an alarm easily, the present invention is not necessarily limited to such a configuration.

FIGS. 5 to 8 show four other embodiments, all of which include the same excitation circuit, electrodes and differential amplifier, as shown in FIG. 2.

Figure 5:
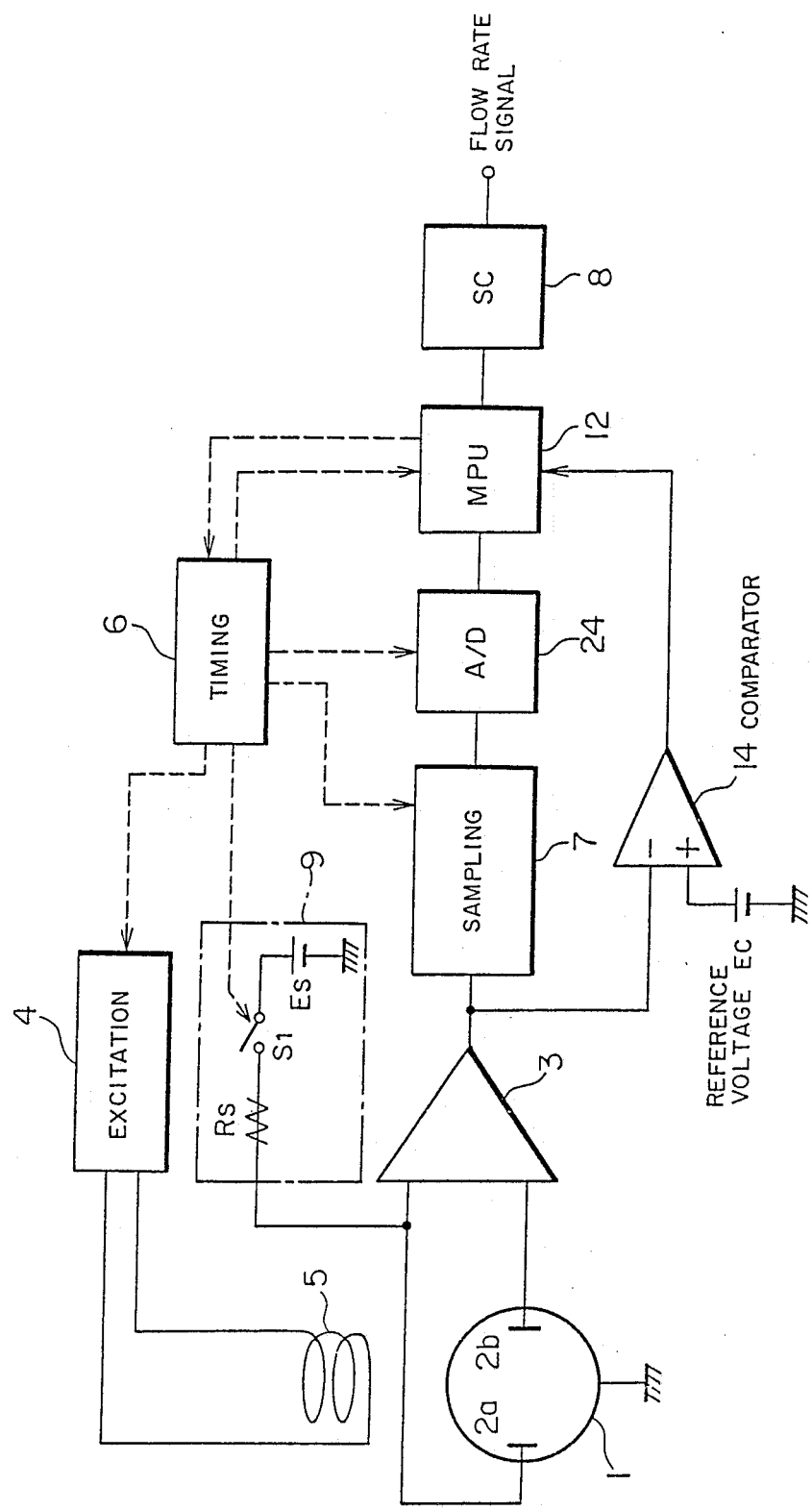
FIG. 5 is a block diagram showing a circuit of an electromagnetic flowmeter, according to a second embodiment of the invention, capable of detecting whether the fluid in a measuring tube has not filled the measuring tube.

According to a second embodiment shown in FIG. 5, an output of the differential amplifier 3 is connected to one of the inputs of a comparator 14, and the other input of the comparator is connected to a reference voltage Ec. This configuration allows it to detect that the electrical resistance Rf of the fluid exceeds a predetermined value from the fact that the output of the comparator 14 is reversed. Upon depletion of the water in the measuring pipe 1, for instance, the electrical resistance Rf of the fluid substantially increases to an infinitely large value, and therefore the voltage drop due to the resistance Rf increases. As a result, the fact that the measuring pipe 1 is not filled with water is detected by appropriately selecting the relationship between the differential amplifier and the reference voltage Ec. More specifically, when the resistance Rf becomes infinitely large (not filled with water), the output of the comparator 14 is reversed in polarity, and upon detection of this operation by the microcomputer 12, a procedure necessary when the pipe is not filled with water, can be taken, such as by producing a water-not-full signal or reducing the flow rate signal to zero. Means for detecting that the measuring pipe is not filled with water can be configured by adding only a pulse injection circuit 9, a comparator 14 and a reference voltage Ec to an ordinary electromagnetic flowmeter, thereby making it possible to monitor water fill normally without interfering with the flow rate measurement.

Unlike in FIG. 5 where the output of the comparator 14 is connected directly to the microcomputer 12, a monostable multivibrator 23 may be connected to the output of the comparator 14 for shaping the waveform.

Figure 6:
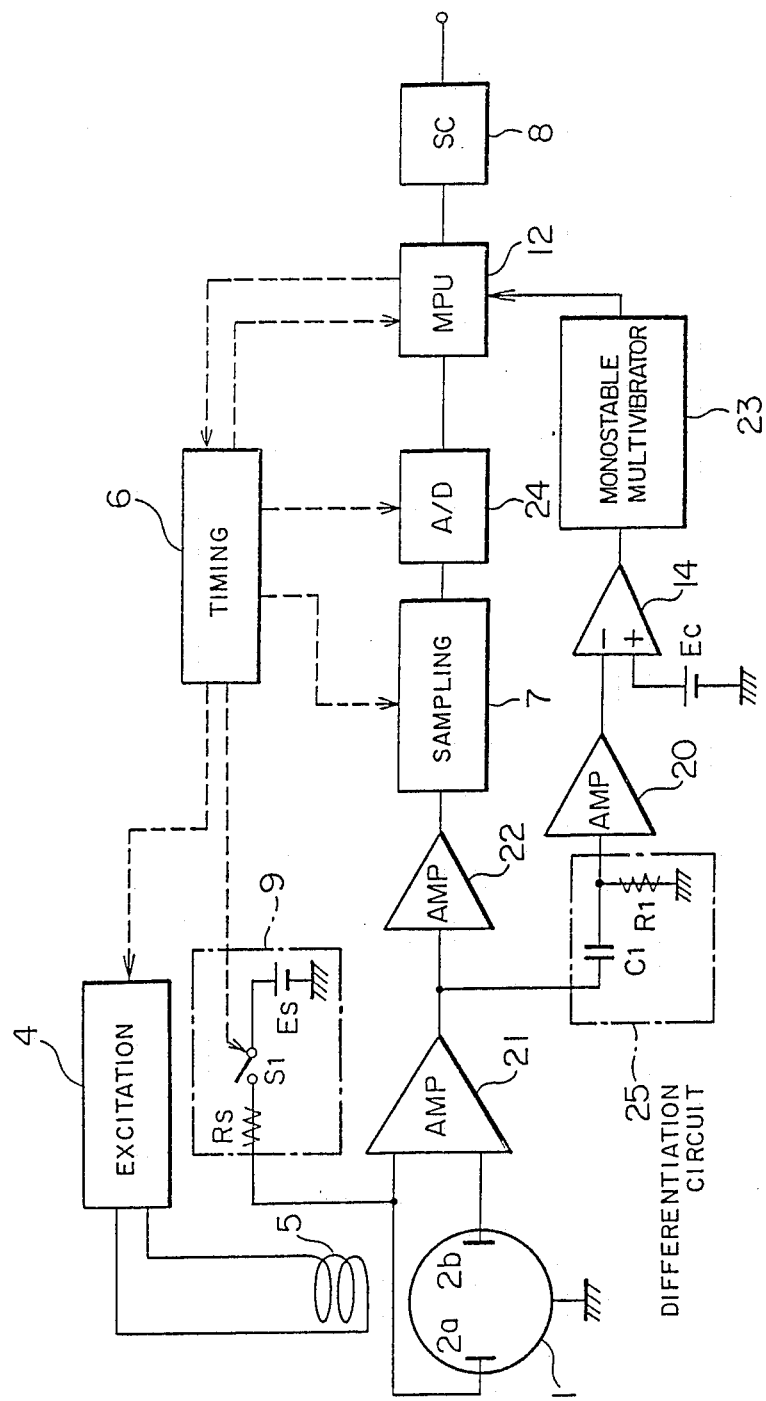
FIG. 6 is a block circuit diagram showing a third embodiment of the present invention in which the false operation of the comparator is prevented under an excessive flow rate.

A third embodiment shown, in FIG. 6, comprises a differentiation circuit 25 including a capacitor C1, a resistor R1 and an amplifier 20 inserted at the input of the comparator 14. Since the differentiation circuit 25 is used for amplification by an amount equal to the voltage drop due to Rf, the comparator 14 is prevented from being falsely operated by a flow rate signal even when the flow rate becomes excessive. In this case, the signal amplifier is preferably divided into a differential amplifier 21 and an amplifier 22 so that the output of the differential amplifier 21 may be connected to the input terminal of the differentiation circuit 25.

Figure 7:
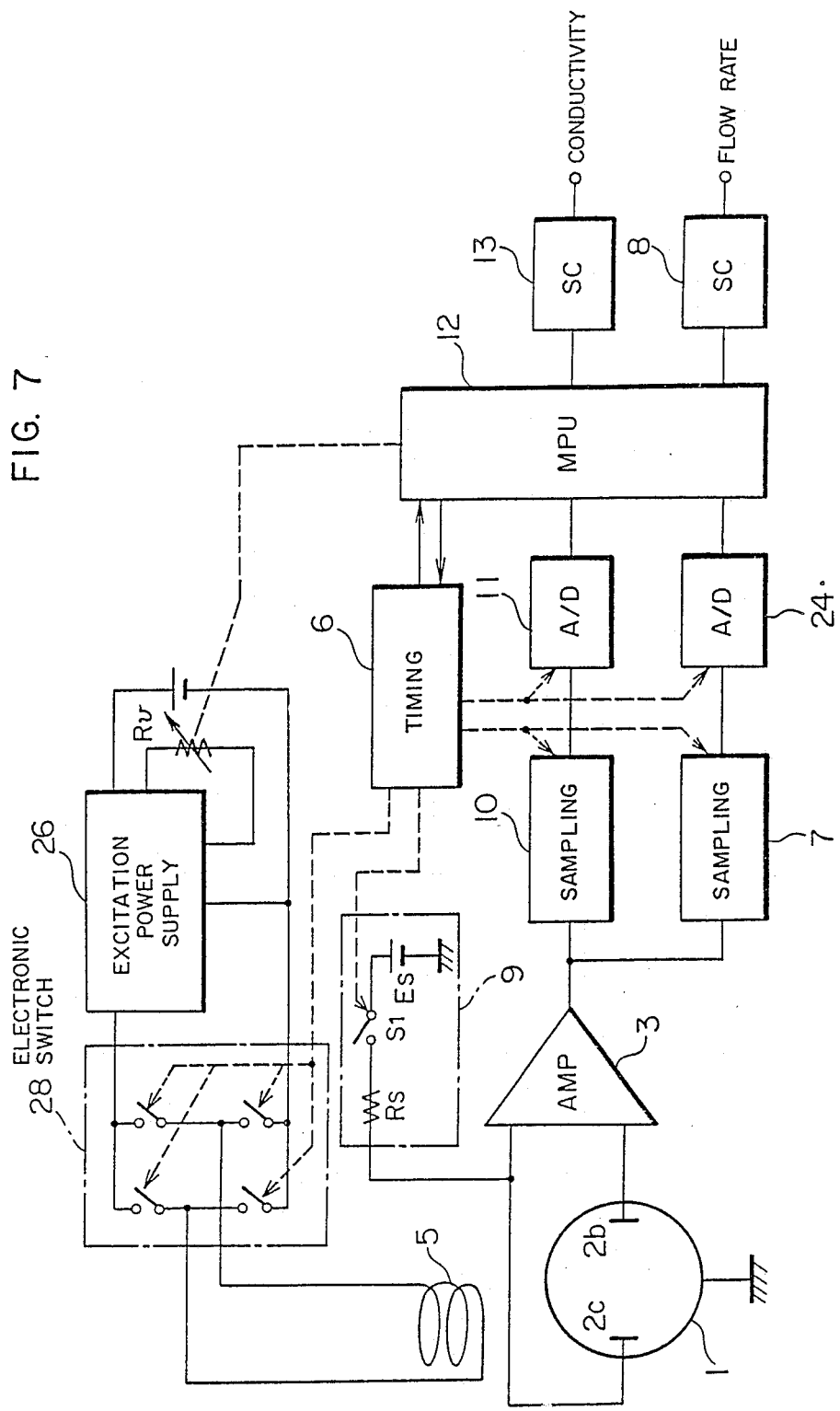
FIG. 7, is a block circuit diagram showing a fourth embodiment of the invention in which the flow rate signal is prevented from fluctuating when the fluid conductivity is decreased.

The fourth embodiment, shown in FIG. 7, is intended to reduce the fluctuation of the flow rate signal by increasing the excitation voltage or the excitation frequency, on the basis of a conductivity signal, when the conductivity of the fluid becomes low.

The circuit of FIG. 7, which is basically identical to that of FIG. 1, differs partly in the method of processing the flow rate signal and the excitation circuit.

The excitation circuit 4 in FIG. 2 is divided into an electronic switch circuit 28 and an excitation power supply 26 with the excitation voltage signal changeable according to the value of the resistor Rv from outside. The value of the resistor may be changed by an analog switch by switching the microcomputer 12.

The sampling circuit 7 shown in FIG. 7, like in FIG. 2, rectifies the flow rate signal synchronously, and after converting the resulting signal into a digital quantity by an A/D converter 24, applies it to the microcomputer 12.

The conductivity signal, on the other hand, is detected in exactly the same manner as in FIG. 2 and is applied to the microcomputer 12. When the conductivity decreases below a predetermined value, the microcomputer 12 changes a voltage-setting resistor Rv of the excitation power supply 26 to increase the excitation voltage, that is, the excitation power.

As a result, the output signal is increased in proportion to the excitation voltage and the ratio S/N is improved, thus reducing the output fluctuation caused by a reduced conductivity. When the excitation voltage is changed, the magnitude of the flow rate signal is also changed, and therefore it is easy to divide the flow rate signal within the microcomputer 12 by a multiple equivalent to the change in excitation voltage.

It is also possible to reduce the fluctuation of the flow rate signal by increasing the excitation frequency. For this purpose, the excitation frequency may be controlled by changing the clock frequency of the timing circuit 6 through the microcomputer 12.

The fifth embodiment, shown in FIG. 8, represents a case employing a residual magnetism method for generating a magnetic field.

In the residual magnetism method, an excitation current in impulse form is supplied to a residual magnetism circuit 27 for a short length of time to generate a rectangular waveform magnetic field. By inserting a resistor R2 between a switch and the negative terminal of a power supply, as shown in the excitation circuit 28 of FIG. 8, it is possible to secure the function equivalent to that of the pulse injection circuit 9 in FIG. 2. The voltage drop across the resistor R2 is injected as an impulse into the electrode 2a through the resistor Rs.

Other operations are exactly the same as those of the other embodiments.

In the aforementioned embodiments, the sampling period for the voltage drop due to Rf is equal to the period during which the switch S1 is turned on as shown by FIG. 3B and FIG. 3E. This is only an example, and the sampling period indicated by FIG. 3E may be either longer or shorter than the length of time the switch S1 is turned on.

Further, the entire waveform of FIG. 3D may be applied to an integration circuit to determine the entire area. In such a case, the flow rate signals are offset with each other as they are opposite in polarity at every half cycle, so that only the voltage drop due to Rf is produced in a manner similar to the embodiment in which the sampling time lasts only while the switch S1 remains on. Considering the offset voltage of the differential amplifier 3, however, the sampling period shown in FIG. 3 is more preferable.

Figure 9A:
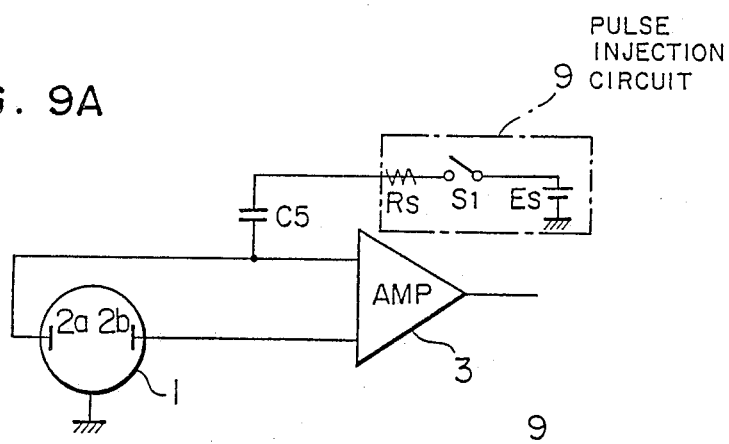
FIGS. 9A to 9C are circuit diagrams showing other embodiments with different pulse injection circuits.
Figure 9B:
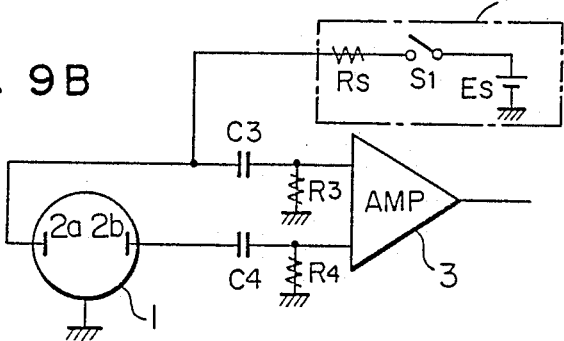
Figure 9C:
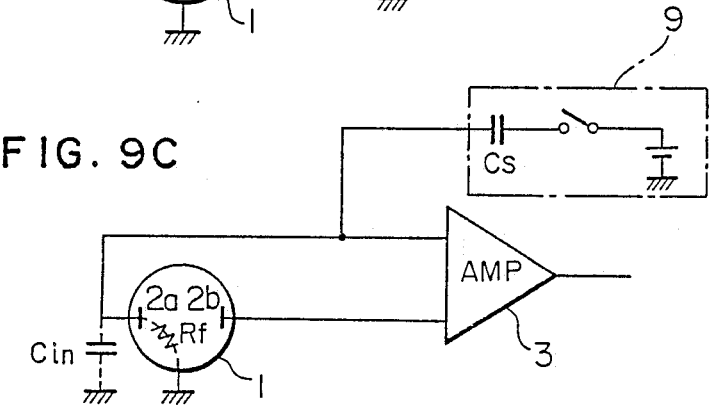

Other embodiments relating to the method of pulse injection are shown in FIGS. 9A to 9C.

FIG. 9A shows a case in which a capacitor C5 is inserted between the pulse injection circuit 9 and one electrode 2a. By insertion of the capacitor C5, even when the pulse injection circuit 9 has a DC offset, only an impulse may be injected and therefore the effect of offset on the differential amplifier 3 is eliminated.

FIG. 9B shows another embodiment in which the differential amplifier 3 is connected to the electrodes through a capacitor C3, a resistor R3, a capacitor C4 and a resistor R4. In this case, a pulse injection circuit 9 is interposed between the capacitor C3 and the electrode 2a to produce the same effect as in other embodiments on one hand, and the differential amplifier 3 is not affected by the fact that the pulse injection circuit 9 has a DC offset, if any, on the other hand.

FIG. 9C shows still another embodiment in which the resistor Rs is replaced by the capacitor Cs in the pulse injection circuit 9. Waveforms produced at various parts of this embodiment are shown in FIGS. 10A–10F.

FIGS. 10A, 10B and 10C correspond to FIGS. 3A, 3B and 3C respectively, and FIGS. 10D, 10E and 10F are similar to those shown in FIG. 3D–F. These waveforms, therefore, will not be explained further.

When the switch S1 is turned on at a timing specified by FIG. 10B, a differentiation waveform as shown in FIG. 10C is produced in the electrode 2a. This waveform is an ideal differentiation waveform formed only of the electrical resistance Rf and the capacitor Cs but with the rise portion thereof made dull under the effect of a very small, stray capacity Rf between the electrodes and the earth which is added to the fluid resistance Rf parallely thereto.

The configuration of FIG. 9C is also identical to those of the other embodiments as far as separation and detection of a flow rate signal and a conductivity signal are concerned after signal amplification. The sampling period of the conductivity signal, however, is preferably equal to or shorter than the turn-on time of the switch S1.

The value of the voltage drop due to Rf is desirably from a value almost equal to the flow rate signal to a value of about one hundred times as great. The voltage drop due to Rf is determined by the ratio between the resistances Rs and Rf, and therefore the resistance Rs is required to be sufficiently large as compared with the electrical resistance Rf of the fluid, or in the range from at least several MΩ to as large as several thousand MΩ in some cases.

A resistor as large as several thousand MΩ is expensive and bulky. If it can be replaced with a small capacitor Cs (several PF to several thousand PF), the cost and size of the instrument can be greatly reduced.

It will be understood from the foregoing description that the following advantages are obtained from the present invention:

(1) Without sacrificing the function of the flow rate measurement of a flowmeter, and making use of almost all circuits thereof, a pulse injection circuit, a sampling circuit 10 and an A/D converter 11 are provided with a small number of parts for separating a flow rate signal and a conductivity signal, such that the two signals can be produced, at the same time, without increasing the cost of the electromagnetic flowmeter.

Simply by installing the electromagnetic flowmeter, the operator can determine both the flow rate and the conductivity (water quality) of the water flowing at a particular position, thus making it possible to monitor the water quality.

This function is very effective in monitoring the introduction of waste water or chemicals that might occur due to an error in connecting a pipe carrying tap water.

Also, as applied to sewage, useful information is obtained as to the required treatment capacity depending on the degree of water pollution.

(2) It is possible to detect whether the conductivity is infinitely large or has exceeded a predetermined level. Upon detection of water fill, the output signal of the electromagnetic flowmeter is forcibly reduced to below zero, thereby preventing the integrating meter at the receiver side of taking an abnormal count or otherwise operating falsely. When there is no fill of water, an ordinary electromagnetic flowmeter produces an inaccurate output from below zero to more than a maximum flow rate and also operates variably with time.

When there is no fill of water, the electromagnetic flowmeter is not required to operate for measurement, and therefore, the power consumption of an electromagnetic flowmeter operating on battery can be remarkably reduced by taking a measure such as turning off the excitation current.

(3) An electromagnetic flowmeter generally has a small fluctuation of an output signal for a fluid of high conductivity and a large fluctuation of an output signal for a fluid of low conductivity.

This fluctuation can be suppressed by increasing the intensity of the excitation magnetic field.

It is also possible to dampen the fluctuation by increasing the excitation frequency. In the case where the fluid has decreased conductivity, for example when a mixture of chemicals is involved, the entire power consumption can be reduced if the fluctuation is dampened by increasing the excitation voltage (or current) or the excitation frequency, only when the conductivity is low.

In the case of a residual magnetism type of excitation system, an increased frequency would increase power consumption. Normally, therefore, the system is operated with a low-frequency excitation, and only when the conductivity is decreased, the excitation frequency is preferably increased in order to reduce the average power consumption and thus lengthen the operation time of a battery, if used for the operation of the system.

I claim:

1. An electromagnetic flowmeter comprising:
   a measuring pipe which is grounded;
   means for generating magnetic fluxes in a pulse form in a direction substantially perpendicular to the direction of flow of a fluid in said measuring pipe;
   a pair of electrodes mounted on the inner wall of said measuring pipe in contact with said fluid for detecting an induced voltage generated in said fluid;
   means for injecting into one of said electrodes an electrical pulse synchronous with a switching timing of said magnetic fluxes in pulse form;
   means for producing a flow rate signal representing the flow rate of said fluid from an output signal produced from said pair of electrodes; and
   means for producing a conductivity signal representing the conductivity of said fluid from an output signal generated from said pair of electrodes.

2. An electromagnetic flowmeter according to claim 1, wherein said means for generating magnetic fluxes in pulse form includes an excitation coil for generating said magnetic fluxes in pulse form, an excitation circuit of generating an excitation current in pulse form in order to excite said excitation coil, a timing circuit for controlling the switching timing of said excitation current of pulse form, and a microcomputer for controlling the timing circuit.

3. An electromagnetic flowmeter according to claim 2, wherein said means for injecting includes an electronic switch controlled by the timing circuit.

4. An electromagnetic flowmeter according to claim 2, wherein said means for producing a conductivity signal includes a sampling circuit for sampling an output signal of said electrodes which is controlled by said timing circuit.

5. An electromagnetic flowmeter comprising:
   a measuring pipe which is grounded;
   means for generating magnetic fluxes in pulse form in a direction substantially perpendicular to the direction of the flow of a fluid in said measuring pipe;
   a pair of electrodes mounted on the inner wall of said measuring pipe in contact with the fluid for detecting an induced voltage generated in the fluid;
   means for injecting into one of said electrodes an electrical pulse synchronous with the switching timing of an excitation current for generating said magnetic fluxes in pulse form;

means for producing a flow rate signal representing the flow rate of said fluid from an output signal of said pair of electrodes; and a comparator for comparing a detected voltage drop across the electrical resistance of said fluid with a predetermined reference voltage.

6. An electromagnetic flowmeter according to claim 5, wherein said means for generating magnetic fluxes in pulse form includes an excitation coil for generating said magnetic fluxes in pulse form, an excitation circuit for generating an excitation current in pulse form to excite said excitation coil, a timing circuit for controlling the switching timing of said excitation current in pulse form and a microcomputer for controlling said timing circuit.

7. An electromagnetic flowmeter according to claim 6, wherein said means for injecting includes an electronic switch controlled by said timing circuit.

8. An electromagnetic flowmeter comprising:

a measuring pipe which is grounded;

means for generating magnetic fluxes in pulse form in a direction substantially perpendicular to the direction of flow of a fluid in said measuring pipe;

a pair of electrodes mounted on the inner wall of said measuring pipe in contact with said fluid for detecting an induced voltage generated in said fluid;

means for injecting into one of said electrodes an electrical pulse synchronous with the switching timing of an excitation current for generating said magnetic fluxes in the pulse form;

means for producing a flow rate signal representing the flow rate of said fluid from an output signal of said pair of electrodes;

means for producing a conductivity signal representing the conductivity of said fluid from an output signal of said pair of electrodes; and an excitation power supply for changing the output of said means for generating said magnetic fluxes in accordance with the magnitude of said conductivity signal.

9. An electromagnetic flowmeter according to claim 8, wherein said means for generating magnetic fluxes in pulse form includes an excitation coil 5 for generating said magnetic fluxes in pulse form; an excitation circuit for generating an excitation current in pulse form in order to generate said magnetic fluxes in pulse form, a timing circuit for controlling the switching timing of said excitation current in pulse form, and a microcomputer for controlling said timing circuit.

10. An electromagnetic flowmeter according to claim 9, wherein said means for injecting includes an electronic switch controlled by said timing circuit.

11. An electromagnetic flowmeter according to claim 9, wherein said means for producing a conductivity signal includes a sampling circuit for sampling an output signal of said electrodes, said sampling circuit being controlled by said timing circuit.

12. An electromagnetic flowmeter according to claim 9, wherein the input of said excitation power supply is changed in accordance with the magnitude of said conductivity signal by said microcomputer.

* * * * *